US00PP27105P3

(12) United States Plant Patent
Bright et al.

(10) Patent No.: US PP27,105 P3
(45) Date of Patent: Aug. 30, 2016

(54) PEACH-ALMOND HYBRID TREE NAMED 'LILLIAN CVI'

(50) Latin Name: ***Prunus* sp.**
Varietal Denomination: Lillian CVI

(71) Applicants: William Bright, Merced, CA (US); Wendy Bright, Merced, CA (US)

(72) Inventors: William Bright, Merced, CA (US); Wendy Bright, Merced, CA (US)

( * ) Notice: Subject to any disclaimer, the term of this patent is extended or adjusted under 35 U.S.C. 154(b) by 169 days.

(21) Appl. No.: 13/998,869

(22) Filed: Dec. 17, 2013

(65) Prior Publication Data

US 2015/0173261 P1 Jun. 18, 2015

(51) Int. Cl.
*A01H 5/08* (2006.01)

(52) U.S. Cl.
USPC ..... Plt./180

(58) Field of Classification Search
USPC ..... Plt./180, 194, 155
See application file for complete search history.

(56) References Cited

U.S. PATENT DOCUMENTS

PP18,782 P3 5/2008 Bright

*Primary Examiner* — Susan McCormick Ewoldt
*Assistant Examiner* — Karen Redden

(57) ABSTRACT

The present invention relates to a peach-almond hybrid tree, *Prunus* sp., and more particularly to a new and distinct variety broadly characterized by a large size, extremely vigorous, hardy, self-sterile, light producing and irregular bearing tree. The nut matures under the ecological conditions described in mid August, with the harvest date on Aug. 10, 2013. The tree is most useful for a commercial rootstock, which has shown to be compatible with all tested almonds. The tree has a strongly developed root system and has shown to be very drought tolerant, very tolerant to excess rain and irrigation, and somewhat resistant to nematodes while having an unknown susceptibility to crown rot, oak root fungus, crown gall, and bacterial canker. As a rootstock, the tree supports very heavy production from budded commercial almond varieties.

1 Drawing Sheet

Botanical classification: *Prunus* sp.
Variety denomination: 'LILLIAN CVI'.

BACKGROUND OF THE VARIETY

In an effort to provide quality rootstocks for fruits and nuts, we, the inventors, typically hybridize and test a large number of almond seedlings each year. The present invention relates to a new and distinct variety of peach-almond hybrid tree, which has been denominated varietally as 'Lillian CVI'.

During the spring of 1988 we crossed several 'Titan' (unpatented) almond trees with peach pollen. This hybridization was accomplished by carefully isolating alternate trees of the 'Titan' almond with several different peach rootstocks. The 'Titan' almond is self-sterile, so the peach rootstocks provided the only available pollen source. That fall the hybridized seeds were gathered and planted as a group in our nursery. Most of the seeds sprouted in the spring of 1989, the young seedlings were then budded to commercial almonds that June, and the resulting trees were transplanted as one of about four thousand trees in our cultivated almond orchard the following winter near Merced, Calif. in Merced County (San Joaquin Valley). After years of observation, the present variety was selected by us as a single plant from the group described above because it showed to be much more vigorous and healthier than its sister seedlings. Subsequent to origination of the present variety of peach-almond hybrid tree, we asexually reproduced it using tissue culture techniques for further testing and evaluation as a potential rootstock. These reproductions revealed that the tree and fruit characteristics were true to the original plant in all respects. Such reproductions were transplanted into our test orchard located a few miles from the original tree and were carefully evaluated. After showing several outstanding characteristics, we determined the variety to have commercial value as a *prunus* rootstock.

The present variety is similar to its selected seed parent, 'Titan' almond by producing almonds that are sweet in flavor with a thin, well sealed shell, but is quite distinguished therefrom by being much more vigorous, by being more tolerant to saline soil types with high ph conditions, by having a much stronger root system for better tree anchorage, and by being a peach-almond hybrid instead of a pure almond.

The variety is most similar to 'Arthur V' (U.S. Plant Pat. No. 18,782) by being a peach almond hybrid tree that is utilized primarily as a rootstock for *prunus* varieties, somewhat nematode resistant, deep rooting, and self-sterile, that has globose leaf glands, and that produces almond-like fruit, but is distinguished therefrom by being more vigorous, by being more tolerant to excess water, by being more drought tolerant, by being more tolerant to saline soil types with high ph conditions, by being less productive of its own fruit, and by having fruit that matures in August instead of September.

SUMMARY OF VARIETY

In summary, the present peach-almond hybrid variety is characterized by a large size, extremely vigorous, hardy, self-sterile, light producing and irregular bearing tree. The nut matures under the ecological conditions described in mid August, with the harvest date on Aug. 10, 2013. The tree is most useful for a commercial rootstock, which has shown to be compatible with all tested almonds. The tree has a strongly developed root system and has shown to be very drought tolerant, very tolerant to excess rain and irrigation, and somewhat resistant to nematodes while having an unknown susceptibility to crown rot, oak root fungus, crown gall, and bacterial canker. As a rootstock, the tree supports very heavy production from budded commercial almond varieties.

DRAWING

The accompanying photograph exhibits three whole fruits positioned to display the characteristics of the hull color and form, one fruit divided along the suture plane to reveal the inside of the hull and the shell, one kernel, and typical leaves.

The photograph also includes three insets revealing a buds and blossoms.

POMOLOGICAL CHARACTERISTICS

Referring now more specifically to the pomological characteristics of this new and distinct variety of peach-almond hybrid tree, the following has been observed under the ecological conditions prevailing near Merced, Merced County (San Joaquin Valley), Calif. The tree and fruit description was developed one week after harvest on Aug. 17, 2013, on a cloned tree during its third growing season in our test orchard located nearby the original selection site. The blossom descriptions were made the previous spring. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

TREE

Size: Large, reaching a height of 13' [3.96 m.] and a spread of 7' [2.13 m.] during its third growing season utilizing minimal dormant pruning.

Vigor: Extremely vigorous. The variety grows about 3' [0.91 m.] of top-growth during the spring and summer.

Growth: Upright and dense.

Form: Pruned to a vase form.

Hardiness: Hardy with respect to central California winters.

Heat tolerance: Observed to perform extremely well in typical central California climatic conditions, which typically include extended periods of heat.

Drought tolerance: Variety requires regular irrigation, but is very tolerable to drought conditions.

Excess water tolerance: Very tolerant to excess rain and irrigation.

Production: Very light.

Fertility: Self-sterile, but may be cross pollinated by an almond, such as 'Nonpareil'(unpatented).

Bearing: Irregular bearer.

Trunk:

- *Size.*—Large, with a maximum diameter of 4½" [114 mm.] during its third growing season.
- *Texture.*—Shaggy.
- *Bark color.*—A Dark grayish yellowish brown [81. d.gy.yBr] and Moderate brown [58. m.Br] variegation.
- *Lenticels.*—Approximate Number Per Square Inch: 16. Color: Light grayish yellowish brown [79. l.gy.yBr]. Size: ⅛" [3.2 mm] to ⅜" [9.5 mm.]. Shape: Elongated to eye-shaped.

Branches:

- *Size.*—Diameter of limb is 2⅛" [54 mm.] measured 8" above the crotch, typical of *Prunus* species, and dependent upon cultural practices and climatic conditions.
- *Texture.*—Medium.
- *Color.*—1st Year Wood Topside: Grayish red [19. gy.R]. 1st Year Wood Underside: Strong yellow green [117. s.YG]. Older Wood: Grayish yellowish brown [80. gy.yBr].
- *Lenticels.*—Approximate Number Per Square Inch: 30. Color: Light yellowish brown [76. l.yBr]. Average size: 3/32" [2.4 mm.]. Shape: Elongated to eye-shaped.

Leaves:

- *Size.*—Large. Average Length: 5⅛" [130 mm.]. Average Width: 1 7/16" [36.5 mm.].
- *Arrangement.*—Alternate.
- *Thickness.*—Medium.
- *Form.*—Elliptical.
- *Apex.*—Acuminate.
- *Base.*—Acute with an average base angle of 80 degrees.
- *Surface.*—Smooth.
- *Color.*—Dorsal Surface: Dark yellowish green [137. d.yG]. Ventral Surface: Moderate olive green [125. m.OlG].
- *Margin.*—Finely serrate.
- *Venation.*—Pinnately net veined.
- *Vein color.*—Light yellow green [119. l.YG].
- *Petiole.*—Average Length: 9/16" [14.3 mm.]. Average Thickness: 1/16" [1.6 mm.]. Color: Strong yellow green [117. s.YG].
- *Stipules.*—Number: Typically 2 per young leaf. Average Length: ¼" [6.4 mm.]. Color: Brilliant yellow green [116. brill.YG] becoming Grayish yellowish brown [80. gy.y.Br] with maturity.
- *Glands.*—Number: Usually 2 to 4, usually occurring in pairs. Position: Slightly alternate with the first pair on the petiole and the rest on the blade base. Size: Small. Form: Globose. Color: Brilliant yellow green [116. brill.YG].
- *Leaf buds.*—Small, pointed, Dark grayish brown [62. d.gy.Br].

Flower buds:

- *Hardiness.*—Hardy, with respect to central California winters.
- *Diameter.*—Typically 5/16" [7.9 mm.] 1 week before bloom.
- *Length.*—Typically 7/16" [11.1 mm.] 1 week before bloom.
- *Form.*—Not appressed.
- *Surface.*—Pubescent.
- *Color.*—Pale pink [7. p.Pk].

Flowers: Perfect, complete, perigynous, usually a single pistil, about thirty stamens, five sepals and petal locations alternately positioned.

- *Type.*—Showy.
- *Average flower diameter.*—1¼" [31.8 mm.].
- *Number of petals.*—Predominately five.
- *Petal shape.*—Oval.
- *Petal margin.*—Somewhat wavy.
- *Average petal diameter.*—9/16" [14.3 mm.].

*Average petal length.*—5/8" [15.9 mm.].
*Petal apex.*—Rounded with an occasional small notch on some.
*Petal base.*—Rounded to obtuse.
*Petal color.*—Pale pink [7. p.Pk] on both sides.
*Anther color.*—Strong orange [50. s.O] over Light yellow [86. l.Y] centers.
*Stigma color.*—Pale greenish yellow [104. p.gY].
*Sepal color.*—Dark purplish red [259. d.pR].
*Sepal length.*—5/16" [7.9 mm.].
*Sepal width.*—3/16" [4.8 mm.].
*Average pistil length.*—5/8" [15.9 mm.].
*Average stamen length.*—1/2" [12.7 mm.].
*Fragrance.*—Moderate.
*Blooming period.*—Medium compared with typical almond varieties.
*Onset of bloom.*—One percent on Feb. 27, 2013.
*Date of full bloom.*—Mar. 10, 2013.
*Duration of bloom.*—One to two weeks, dependent on ambient temperature.
*Number per cluster.*—1 to 3 with single flowers most common.

FRUIT

Maturity when described: One week after harvest, Aug. 17, 2013.
Date of harvest: Aug. 10, 2013.
Form: Uniform, symmetrical, oblong.
*Longitudinal section form.*—Oval.
*Transverse section through diameter.*—Round to elliptical.

HULL

Outer surface: Smooth at hull split, roughens upon drying, pubescent.
Average thickness: 3/32" [2.4 mm.] when dry.
External color: Grayish yellow [90. gy.Y] when dry.
Dehiscence: Opens freely.
Splitting: Complete along the suture.
Adherence: Hulls are easily separated from in-shell nuts.
Texture: Tough and leathery.
Nut cavity: Oval.
*Surface.*—Rough.
*Color.*—Dark orange yellow [72. d.OY] when dry.

SHELL

Type: Freestone.
Form: Oval.
Hilum: Narrow, oval.
Base: Truncate.
Apex: Acute to acuminate.
Sides: Equal.
Surface: Rough, pitted throughout.
External surface color: Light yellowish brown [76. l.yBr].
Cavity surface color: Light yellowish brown [76. l.yBr].
Average width: 13/16" [20.6 mm.].
Average length: 1 1/2" [38.1 mm.].
Average breadth: 7/16" [11.1 mm.].
Average pit wall thickness: 3/64" [1.2 mm.].

KERNEL

Size: Medium.
*Average length.*—7/8" [22.2 mm].
*Average width.*—9/16" [14.3 mm].
*Average thickness.*—1/4" [6.4 mm].
*Average weight.*—32 nuts per ounce [0.89 grams per nut].
Form: Symmetrical.
*Longitudinal section form.*—Ovate.
*Transverse section form.*—Elliptical.
Base: Rounded to Oblique.
Apex: Acuminant with a very sharp tip.
Surface: Slightly wrinkled.
Skin color: Moderate orange yellow [71. m.OY].
Pellicle color: Light grayish brown [60. l.gyBr].
Vein color: Strong brown [55. s.Br].
Number of doubles: Rare.
Taste: Mild and sweet.
Viable: Yes.
Blanchable: Yes.
Percentage of kernel to shell: 55 percent when fully dry.

USE

Rootstock: Can be used as a rootstock for almost all *prunus* varieties, especially almonds.
Flesh: Can be used for cattle feed when dry.
Kernel: Can be used as an almond for human consumption.
Resistance to pests: Somewhat resistant to nematodes.
Resistance to diseases: Unknown tolerances to bacterial canker, crown gall, and oak root fungus.

OTHER NOTES

Although the new variety of peach-almond hybrid tree possesses the described characteristics under the ecological conditions at Merced, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach-almond hybrid tree, substantially as illustrated and described, that is most similar to 'Arthur V' (U.S. Plant Pat. No. 18,782) by being a peach almond hybrid tree that is utilized primarily as a rootstock for *prunus* varieties, somewhat nematode resistant, deep rooting, and self-sterile, that has globose leaf glands, and that produces almond-like fruit, but is distinguished therefrom by being more vigorous, by being more tolerant to excess water, by being more drought tolerant, by being more tolerant to saline soil types with high ph conditions, by being less productive of its own fruit, and by having fruit that matures in August instead of September.

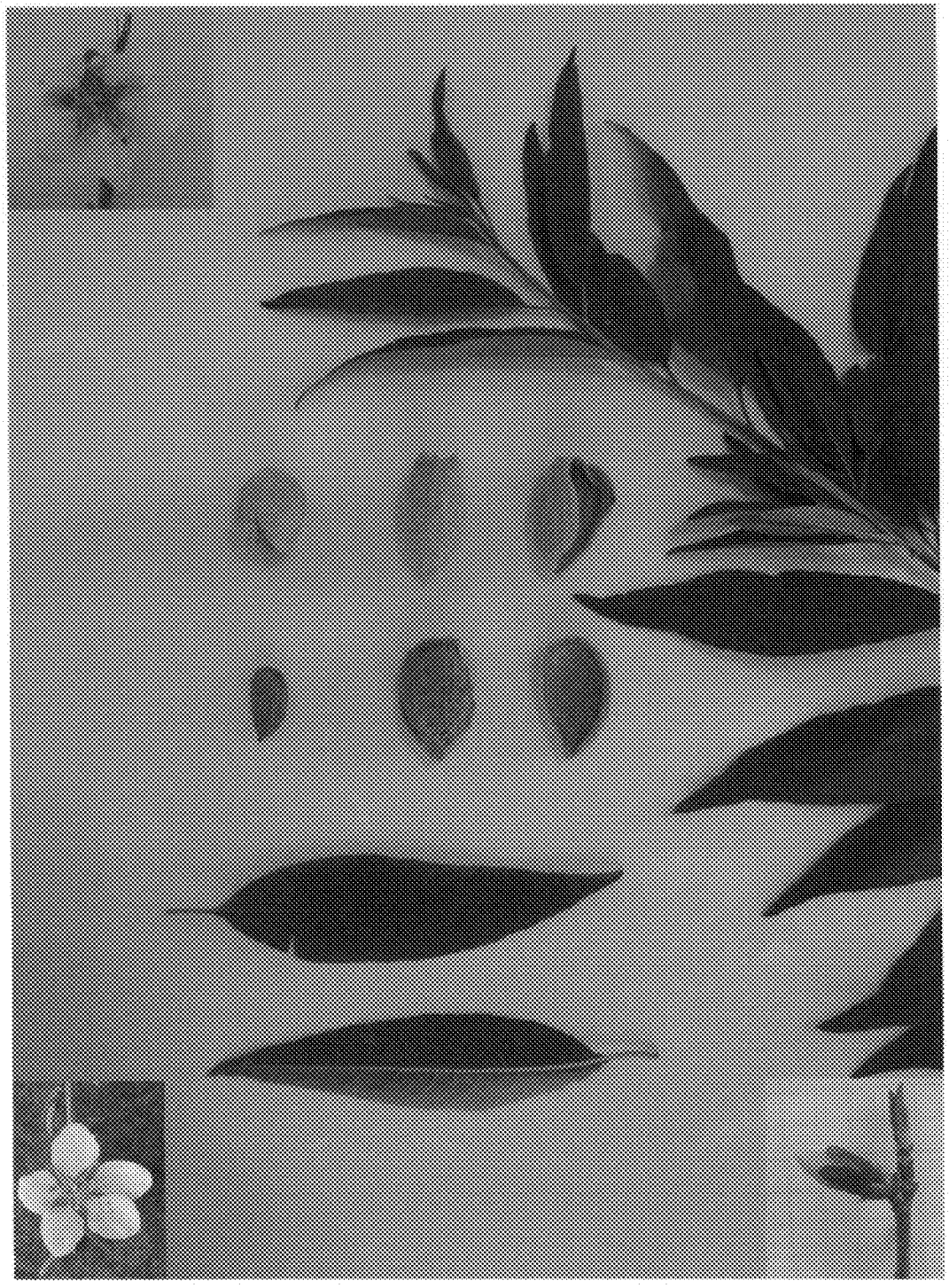

* * * * *